(12) United States Patent
West

(10) Patent No.: US 9,386,910 B2
(45) Date of Patent: Jul. 12, 2016

(54) ENDOSCOPE OVERTUBE FOR INSERTION THROUGH A NATURAL BODY ORIFICE

(75) Inventor: Stephen West, Austin, TX (US)

(73) Assignee: Apollo Endosurgery, Inc., Austin, TX (US)

( * ) Notice: Subject to any disclaimer, the term of this patent is extended or adjusted under 35 U.S.C. 154(b) by 1002 days.

(21) Appl. No.: 13/551,942

(22) Filed: Jul. 18, 2012

(65) Prior Publication Data

US 2014/0024896 A1  Jan. 23, 2014

(51) Int. Cl.
| | | |
|---|---|---|
| A61M 5/178 | (2006.01) |
| A61M 25/00 | (2006.01) |
| A61B 1/00 | (2006.01) |
| A61B 1/12 | (2006.01) |
| A61B 1/273 | (2006.01) |
| G02B 23/24 | (2006.01) |
| A61B 17/34 | (2006.01) |

(Continued)

(52) U.S. Cl.
CPC ......... *A61B 1/00135* (2013.01); *A61B 1/0014* (2013.01); *A61B 1/00128* (2013.01); *A61B 1/12* (2013.01); *A61B 1/2736* (2013.01); *A61B 17/3415* (2013.01); *A61B 17/3439* (2013.01); *A61B 17/3462* (2013.01); *A61B 2017/345* (2013.01); *A61B 2017/347* (2013.01); *A61M 39/0613* (2013.01); *A61M 39/228* (2013.01); *A61M 2039/0673* (2013.01); *G02B 23/2476* (2013.01)

(58) Field of Classification Search
USPC ......... 600/104, 106, 107, 114–116, 121–125, 600/207; 604/93.01, 164.01–164.11, 604/167.01–167.06, 256, 264, 278, 27, 604/96.01–99.04, 171, 172, 246, 523–528, 604/165.01–165.04
See application file for complete search history.

(56) References Cited

U.S. PATENT DOCUMENTS

| | | |
|---|---|---|
| 2,325,831 A | 8/1943 | Cameron |
| 3,057,345 A | 10/1962 | Ferris et al. |

(Continued)

FOREIGN PATENT DOCUMENTS

| | | |
|---|---|---|
| EP | 0397794 | 5/1993 |
| EP | 1505913 | 4/2012 |

(Continued)

OTHER PUBLICATIONS

"Overtube Use in Gastrointestinal Endoscopy", Gastrointestinal Endoscopy, 2009, vol. 70, No. 5, pp. 828-834.

(Continued)

*Primary Examiner* — Ryan Henderson
(74) *Attorney, Agent, or Firm* — Gordon & Jacobson, P.C.

(57) ABSTRACT

An endoscope overtube includes a flexible tubular member and a hub assembly provided at the proximal end of the tubular member. The hub assembly includes an elastic sleeve seal cuff extending about the inner surface of a body member of the hub. The ends of seal cuff are coupled to the body member. An inflation line extends into the body member in communication with the outer surface of the seal cuff. When fluid is pressurized through the inflation line, the cuff is distended inward to reduce the size of the opening through the port such that the cuff forms a seal about an endoscope received through the hub. The body member is preferably coupled to each of the flexible tubular member and to the elastic seal cuff using a snap-fit engagement of parts such that no fasteners, welds, glues, etc. are necessary for securing the hub assembly together.

22 Claims, 3 Drawing Sheets

(51) Int. Cl.
*A61M 39/06* (2006.01)
*A61M 39/22* (2006.01)

(56) References Cited

U.S. PATENT DOCUMENTS

| | | | |
|---|---|---|---|
| 4,875,468 | A | 10/1989 | Krauter et al. |
| 4,900,306 | A | 2/1990 | Quinn et al. |
| 5,161,773 | A * | 11/1992 | Tower ................................ 251/5 |
| 5,423,848 | A | 6/1995 | Washizuka et al. |
| 5,556,367 | A | 9/1996 | Yabe et al. |
| 5,620,408 | A | 4/1997 | Vennes et al. |
| 5,704,926 | A * | 1/1998 | Sutton ........................... 604/526 |
| 6,174,280 | B1 | 1/2001 | Oneda et al. |
| 6,530,881 | B1 | 3/2003 | Ailinger et al. |
| 6,790,173 | B2 | 9/2004 | Saadat et al. |
| 6,814,697 | B2 | 11/2004 | Ouchi |
| 6,869,393 | B2 | 3/2005 | Butler |
| 6,899,672 | B2 | 5/2005 | Chin et al. |
| 7,264,588 | B2 | 9/2007 | Voloshin et al. |
| 7,306,614 | B2 | 12/2007 | Weller et al. |
| 7,905,830 | B2 | 3/2011 | Stefanchik et al. |
| 8,012,086 | B2 | 9/2011 | Ortiz et al. |
| 8,021,293 | B2 | 9/2011 | Dejima et al. |
| 2005/0049460 | A1 * | 3/2005 | Mikkaichi et al. ............ 600/121 |
| 2006/0047183 | A1 | 3/2006 | Park |
| 2007/0203393 | A1 | 8/2007 | Stefanchik |
| 2007/0255101 | A1 | 11/2007 | Bar-Or |
| 2008/0097157 | A1 | 4/2008 | Ortiz et al. |
| 2008/0109028 | A1 * | 5/2008 | Styrc ............................. 606/194 |
| 2010/0010298 | A1 | 1/2010 | Bakos et al. |
| 2010/0010299 | A1 | 1/2010 | Bakos et al. |
| 2010/0076451 | A1 | 3/2010 | Zwolinski et al. |
| 2010/0121144 | A1 | 5/2010 | Farhadi |
| 2010/0298642 | A1 | 11/2010 | Trusty et al. |
| 2010/0331625 | A1 | 12/2010 | Rosemurgy et al. |

FOREIGN PATENT DOCUMENTS

| | | |
|---|---|---|
| WO | WO 89/06529 | 7/1989 |
| WO | WO 92/11880 | 7/1992 |
| WO | WO 99/17665 | 4/1999 |
| WO | WO 03/099140 | 12/2003 |
| WO | WO 2009/122395 | 10/2009 |

OTHER PUBLICATIONS

"Overtubes in Gastrointestinal Endoscopy", Christopher D. Wells, M.D. et al., American Journal of Gastroenterology, 2008; 103:745-752.

* cited by examiner

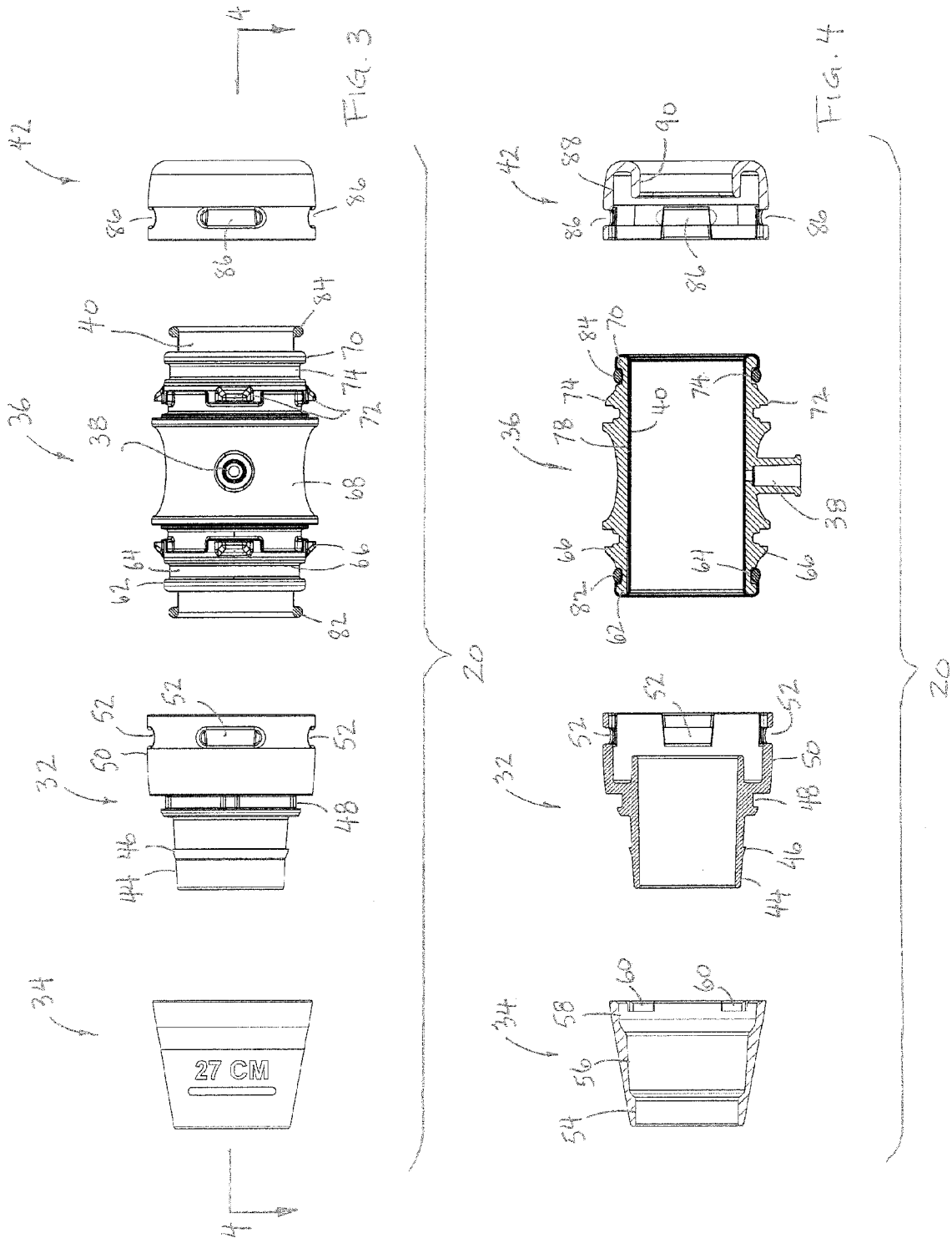

ENDOSCOPE OVERTUBE FOR INSERTION THROUGH A NATURAL BODY ORIFICE

BACKGROUND OF THE INVENTION

1. Field of the Invention

The present invention relates to surgery. More particularly, the invention relates to an access port for providing secure access through a natural body orifice for an endoscope and related instruments.

2. State of the Art

The field of gastrointestinal endoscopy is generally directed to diagnostic and therapeutic techniques to observe, modify and remove tissues located in the digestive tract. Such diagnosis is often performed with an endoscope that is inserted into the mouth of a patient, through the esophagus, and into the stomach. Flexible endoscopic instruments are then advanced through one or more working channels of the endoscope to act on tissues within the stomach.

Depending on the procedure performed, the endoscope can be used in conjunction with an overtube. An overtube is a tubular device that facilitates endoscopy by providing a conduit through which the endoscope can be advanced. The use of the overtube protects the gastrointestinal mucosa from trauma and limits risks of aspiration. This is particularly important where access is required to be maintained for repeated withdrawal and reinsertion of the endoscope during certain procedures, such as foreign body removal, multiple biopsy, or procedures requiring instrument exchange which may occur external the endoscope or require withdrawal of the endoscope.

SUMMARY OF THE INVENTION

According to embodiments of the invention, an endoscope overtube is provided that facilitates intraluminal access by an endoscope through a natural orifice, such as the digestive tract. The overtube generally includes a flexible tubular member, and a hub assembly provided at the proximal end of the flexible tube.

The tubular member has a length sufficient to extend from the mouth, through the alimentary canal and to the stomach of the patient. The tubular member is laterally flexible, but reinforced to remain patent and longitudinally stiff under conditions of use. The tubular member defines a central passage for receiving the endoscope, and a resilient and flexible tapered distal tip dimensioned to engage the exterior of the endoscope passed within the central passage.

According to one aspect of the invention, the hub assembly is provided with an elastic tubular sleeve-like seal cuff extending about the inner surface of a body member of the hub. The proximal and distal ends of seal cuff are coupled in a fluidtight manner to the body member, with an outer surface of the seal cuff in opposition to the inner surface of the body member, and an inner surface of the seal cuff exposed within the body member. An inflation line extends into the body member in communication with the outer surface of the seal cuff. When fluid is provided under pressure through the inflation line and between the inner surface of the body member and outer surface of the cuff, the cuff is distended radially inward away from the inner surface of the body member into an expanded configuration that reduces the size of the opening through the port. More particularly, when an endoscope is received through the hub and the cuff is expanded under pressure, the cuff forms a seal about the endoscope.

According to another aspect of the invention, the body member is coupled to each of the flexible tubular member and to the elastic seal cuff using a snap-fit engagement of parts such that no fasteners, welds, glues, etc. are necessary for securing the hub assembly together. More particularly, the hub assembly includes an inner collar and an outer collar between which the proximal end of the flexible tubular member is secured by engagement of the inner and outer collars. The hub assembly also includes a proximal end cap that fixes the proximal end of the seal cuff relative to the body member by engagement of the cap to the body member, and the inner collar engages relative to the distal end of the body member to fix the distal end of the sleeve relative to the body member. According to a preferred aspect of the invention, the body member is longitudinally symmetrical such that either end of the body member may be the proximal end or distal end, thereby aiding assembly.

Additional objects and advantages of the invention will become apparent to those skilled in the art upon reference to the detailed description taken in conjunction with the provided figures.

BRIEF DESCRIPTION OF THE DRAWINGS

FIG. 3 is an assembly view of the hub of the overtube.

FIG. 4 is a longitudinal section view across line 4-4 in FIG. 3.

FIG. 5 is a side elevation view of the overtube coupled to an inflation system.

FIG. 6 is illustrates the inflation of the seal cuff of the overtube by the inflation system.

DETAILED DESCRIPTION OF THE PREFERRED EMBODIMENTS

With reference to the following description, the terms "proximal" and "distal" are defined in reference to the hand of a user of the device, with the term "proximal" being closer to the user's hand, and the term "distal" being further from the user's hand such as to often be located further within a body of the patient during use.

Figure 1:
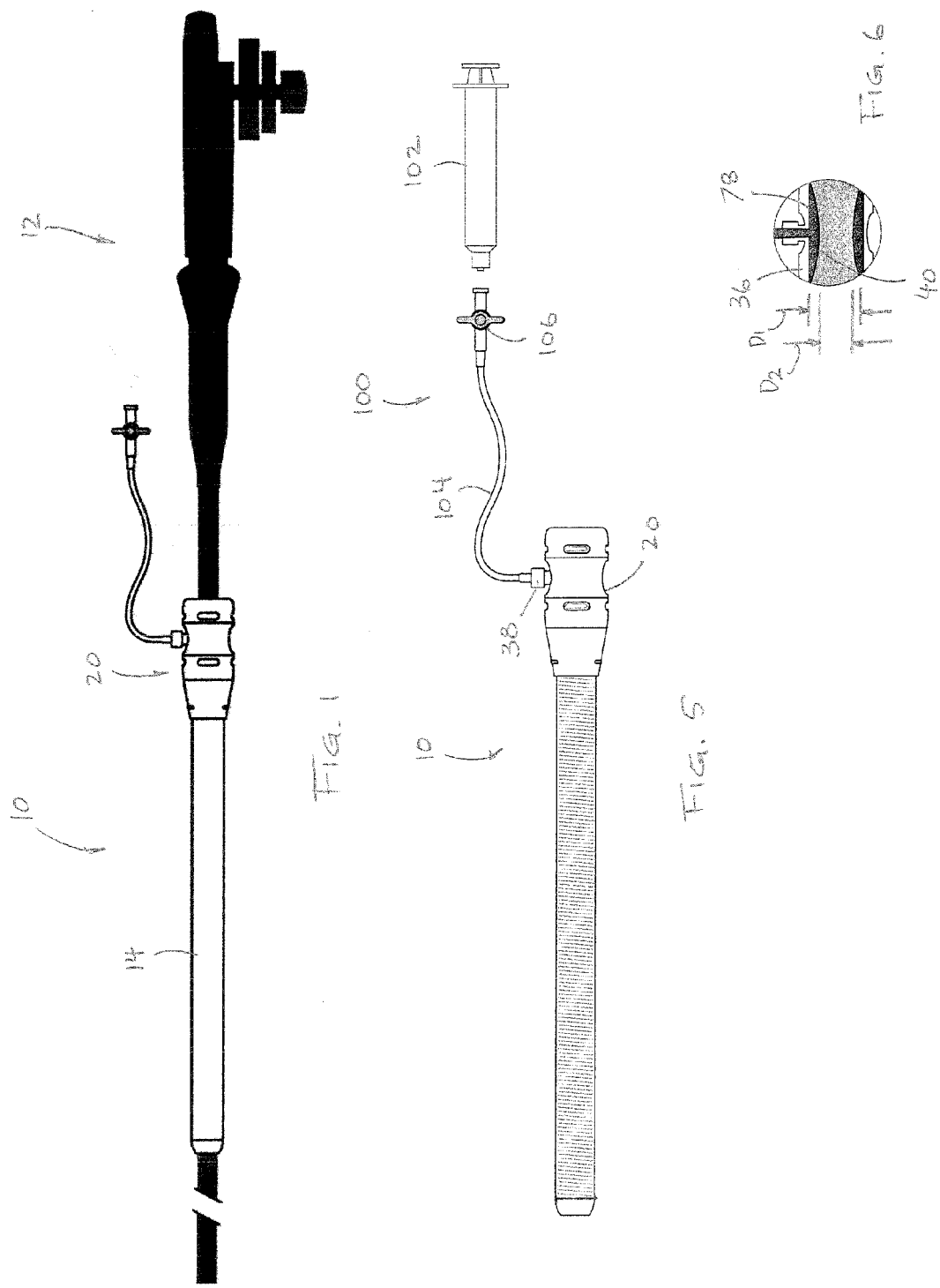
FIG. 1 is a side elevation view of an overtube according to the invention, with an endoscope shown in silhouette extending through the overtube.

Turning now to FIG. 1, in accord with the invention, an overtube 10 is provided for facilitating access, guidance, and intubation of an endoscope 12 and various endoscopic instruments into a natural orifice of a patient for intraluminal procedures. The overtube is particularly intended for use in various procedures in which it is inserted through the esophagus or the colonic passage, but may have other uses such as intravaginal procedures. In addition, once the endoscope is inserted into the overtube 10, the overtube can be operated to provide a seal about the endoscope 12 that maintains a condition of insufflation within a body cavity of the patient, as described in more detail below.

Figure 2:
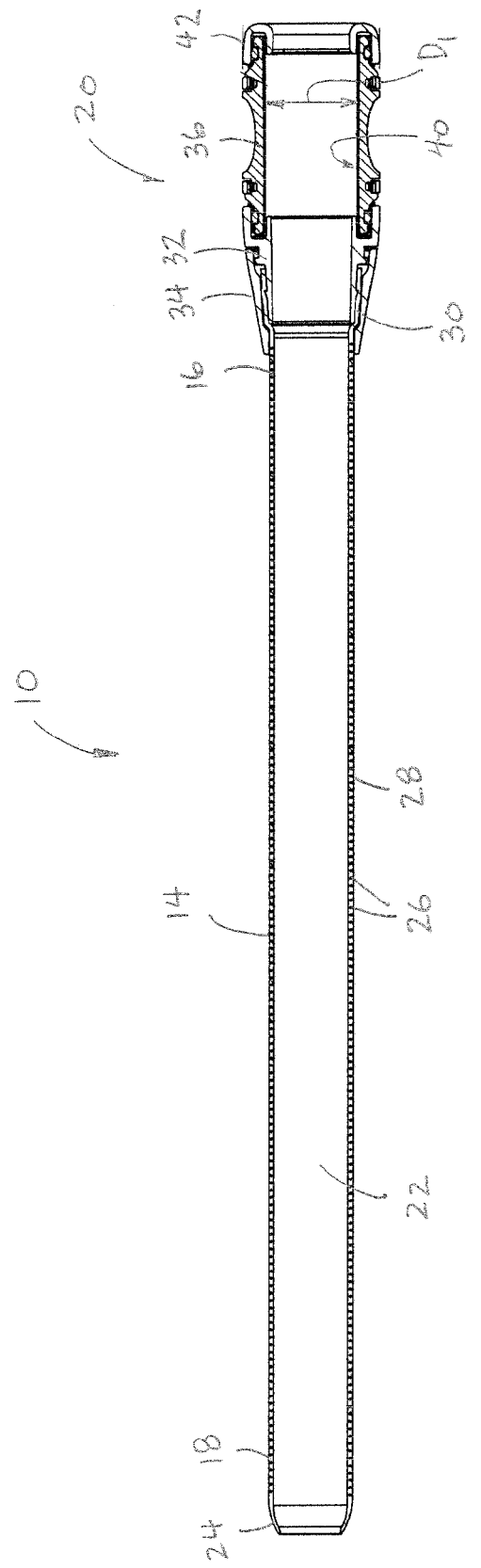
FIG. 2 is a longitudinal section view through the overtube of FIG. 1.

Referring to FIG. 2, the overtube 10 includes an elongate flexible tubular member 14 having a proximal end 16 and a distal end 18, and a hub 20 provided at the proximal end 16 of the tubular member 14. In a preferred embodiment, the tubular member 14 has a length sufficient to extend from the mouth, through the alimentary canal and to the stomach of the patient, e.g., approximately 27 cm, however the tubular member can be provided in other lengths suitable for a particular procedure and the respective intraluminal passage. The tubular member 14 defines a central passage 22 through which the endoscope 12 is received, and includes a resilient and flexible distal tip 24 at its distal end 18 that tapers to a close fitting diameter for the outer diameter of the endoscope(s) 12 for which the overtube 10 is intended to be used. By way of example only, an embodiment of the overtube is designed to accommodate endoscopes having an outer diameter between 10 to 14 mm, defines a central tubular passage 22 with a diameter of 17 mm, and has a distal tip 24 that tapers to a diameter of approximately 11 mm. The tubular member 14 is preferably a polymeric extrusion reinforced with a metal spring wire coil 26 extending through or along its wall 28 for the length of the extrusion, except at its distal tip 24 where increased flexibility is desired and at a proximal coupling portion 30. The tubular member construction is laterally flexible, but sufficiently reinforced to remain patent and longitudinally stiff during insertion into a natural orifice and under conditions of use. To accommodate the various diameter endoscopes, while minimizing the gap between the diameters of the overtube 10 and endoscope 12 that may potentially trap tissue, the distal tip 24 is preferably formed of a resilient material having elastic properties and may be integrally formed or joined to tubular member 14.

Referring to FIGS. 2 through 4, according to one aspect of the invention, the hub 20 is an assembly of five components including an inner tube collar 32 and an outer tube collar 34 that together engage the proximal coupling portion 30 of the tubular member 14, a tubular body member 36 provided with a fluid line connector 38, a sleeve-like sealing cuff 40 extending through the body member 36, and a hub collar 42 coupled to a proximal end of the body member 36. In a preferred assembly of such components, the body member 36 is coupled to each of the tubular member 14 and to the sealing cuff 40 using a snap-fit engagement of inner and outer tube collars 32, 34 at its distal end, and the hub collar 42 at its proximal end, such that no fasteners, welds, glues, etc. are necessary for securing the hub assembly together, as well as securing the hub assembly 20 to the tubular member 14.

More particularly, the inner tube collar 32 includes a tubular portion 44 including a barb 46, a central circumferential retaining groove 48, and a relatively larger diameter proximal flange 50 including a plurality of radially displaced engagement windows 52. The outer tube collar 34 includes a distal tubular portion 54 sized to closely receive the proximal coupling portion 30 of the flexible tubular member 14, a larger diameter central portion 56 sized to receive the tubular portion 44 of the inner collar 32, and a relatively larger diameter proximal portion 58 provided with catches 60 to engage the retaining groove 48 of the inner collar 32 to mechanically engage the inner and outer collars 32, 34 relative to each other. In assembly, the tubular portion 44 of the inner collar 32 is inserted into the proximal coupling portion 30 of the tubular member 14 with the barb 46 making positive engagement within the inner surface of the tubular member. The outer collar 34 is advanced over the tubular member 14 such that the tubular portion 14 of the inner collar 32 extends to the end of the central portion 56 of the outer collar 34 and the catches 60 engage the retaining groove 48 to lock the collars 32, 34 together about the tubular member 14. The tubular member 14 is locked to the inner and outer collars 32, 34 by the tight interference fit created and the positive engagement of the barb 46 against the inner surface of the tubular member 14 and the outer collar 34 over the outside of the tubular member.

The body member 36 includes a first end 62 defining a first circumferential groove 64 and a first plurality of catch barbs 66, a central portion 68, and a second end 70 defining a second plurality of catch barbs 72 and a second circumferential groove 74. The central portion 68 is preferably concave about its circumference to facilitate manual gripping thereof. The fluid line connector 38 is preferably in the form of a leur connector and extends radially outward from the central portion 68 and communicates with a smooth tubular interior 78 of the body member 36. The tubular interior 78 defines a first diameter D1 generally slightly larger than the diameter of the central passage 22. In accord with a preferred aspect of the invention, the body member 36 is longitudinally symmetrical such that either the first or second ends 62, 70 of the body member 36 may be the proximal or distal end for connection to either the inner collar 32 and hub collar 42, as described below, thereby aiding assembly.

The sleeve-like elastic seal cuff 40 extends through the tubular interior 78 of the body member 36 and has ends each defining an O-ring 82, 84. The seal cuff 40 is preferably made from polyisoprene or latex, though other elastic materials may be used. The O-rings 82, 84 may be joined to ends of seal cuff 40 or preferably integrally formed by rolling the ends of the sleeve-like elastic seal cuff 40. The ends of the seal cuff 40 are everted over the first and second ends 62, 70 of the body member 36 with the O-rings 82, 84 seated in first and second grooves 64, 74, respectively, as shown in FIG. 4. The first end 62 of the body member 36 is then inserted into the flange 50 of the inner collar 32 in sufficient close tolerance such that first O-ring 82 of the seal cuff 40 is locked within groove 64, and such that the first plurality of catch barbs 66 extend through engagement windows 52 to lock the body member 36 relative to the inner collar 32 and thus relative to the tubular member 14.

The hub collar 42 is a tubular portion defining a plurality of engagement windows 86, a locking surface 88, and an inverted portion forming a hub mouth 90. The hub collar 42 is positioned over the second end 70 of the body member 36 such that the second plurality of catch barbs 72 extend through the engagement windows 86 to lock the hub collar 42 relative to the body member 36, the locking surface 88 abuts the O-ring 84 to secure it within the second groove 74, and the hub mouth defines a proximal entry into the overtube 10.

Turning to FIGS. 1 and 5, with the assembled overtube 10, an inflation device 100 may be coupled to the fluid connector 38 of the hub 20. One exemplar inflation device 100 includes a syringe 102 for generating fluid pressure, a fluid line 104 for communicating the fluid pressure to the fluid connector 38, and a stopcock 106 for maintaining a fluid pressure. When fluid, such as air, is provided under pressure from the inflation device 100, the fluid enters between the smooth interior 78 of the body member 36 and the outer surface of the seal cuff 40, causing radially inward distension of a central portion of the seal cuff within the body member 36, such that the seal cuff defines a second hub diameter D2 smaller than the first hub diameter D1, as shown in FIG. 6. This creates a seal about an endoscope 12 inserted through the hub 20 of the overtube 10 to prevent loss of pressure in the body cavity when insufflation is used in a surgical or diagnostic procedure. Once the seal is effected, the stopcock 106 can be rotated to maintain the pressure and seal. When it is desired or necessary to remove the endoscope from the overtube, e.g., for removing a tissue sample at the end of the endoscope or at the end of a procedure, the stopcock 106 is rotated to release the pressure and deactivate the seal. The syringe 102 is then preferably operated to withdraw all, or substantially all, fluid from between the seal cuff 40 and the body member 36 to allow the endoscope 12 to be freely removed from the overtube 10.

There have been described and illustrated herein an overtube for an endoscope for use through a natural body orifice such as a mouth. While a particular embodiment of the invention has been described, it is not intended that the invention be limited thereto, as it is intended that the invention be as broad in scope as the art will allow and that the specification be read likewise. Thus, while particular structure for coupling the various elements of the hub together have been described, it will be appreciated that other preferably snap-fit engagement structure can be used as well. It will therefore be appreciated by those skilled in the art that yet other modifications could be made to the provided invention without deviating from its spirit and scope as claimed.

What is claimed is:

1. An overtube for use with an endoscope and for insertion through a patient's natural body orifice, said overtube comprising:
   a) a tubular member having a proximal portion and a distal portion, and a length therebetween sufficient to extend from a patient's mouth to a patient's stomach, said tubular member defining a central passage for receiving the endoscope therethrough; and
   b) a hub assembly coupled to said proximal portion of said tubular member, said hub assembly including
      a rigid body member having an inner surface defining an interior opening with a first diameter, an exterior surface, and a fluid connector,
      a flexible sleeve extending within said inner surface of said body member, said sleeve having an outer surface, an inner surface, and first and second ends, said first and second ends coupled relative to said body member, with said first and second ends of said sleeve everted onto the exterior surface of said body member and fixed relative to said body member, and said outer surface of said sleeve and said inner surface of said body member are in communication with said fluid connector,
      a tube collar assembly coupled at said first end of said body member, said tube collar assembly connecting said tubular member relative to said hub assembly, and including an inner collar that partly extends into said proximal portion of said tubular member, and an outer collar that extends over said proximal portion of said tubular member and said inner collar to fixedly engage said proximal portion of said tubular member between and to said inner and outer collars, said inner and outer collars directly connected together, and
      wherein when a fluid is provided under pressure through said fluid connector, said sleeve distends radially inward to define a second diameter smaller than said first diameter such that when the endoscope is inserted through the hub and the sleeve distends to define the second diameter, the sleeve is provided in contact about an exterior surface of the endoscope.

2. An overtube according to claim 1, wherein:
   when there is no fluid between said outer surface of said sleeve and said inner surface of said body member, said outer surface of said sleeve is in contact with said inner surface of said body member along substantially an entirety of said central passage, and
   when fluid is provided between said outer surface of said sleeve and said inner surface of said body member, said outer surface of said sleeve at least along a longitudinally central portion of said sleeve is displaced from said inner surface of said body member.

3. An overtube according to claim 1, wherein:
   said first and second ends of said sleeve are provided with respective first and second O-rings, and said body member includes first and second ends defining respective first and second circumferential grooves, and said first O-ring is received in said first circumferential groove, and said second O-ring is received in said second circumferential groove.

4. An overtube according to claim 3, wherein:
   said first and second circumferential grooves are located on an exterior surface of said body member.

5. An overtube according to claim 1, wherein said hub assembly further a hub collar coupled at said second end of said body member.

6. An overtube according to claim 4, wherein:
   said first O-ring is secured in said first groove by said tube collar assembly, and said second O-ring is secured in said second groove by a hub collar at said second end of said body member.

7. An overtube according to claim 5, wherein:
   said hub collar is snap fit to said second end of said body member.

8. An overtube according to claim 1, wherein:
   said body member is longitudinally symmetrical.

9. An overtube according to claim 1, wherein:
   said tubular member is reinforced to remain patent and longitudinally stiff during insertion into the natural orifice, while remaining sufficiently laterally flexible for insertion through a non-straight natural orifice.

10. An overtube according to claim 1, wherein:
    said tubular member comprises a polymer reinforced with a metal coil.

11. An overtube according to claim 1, wherein:
    said sleeve is elastic.

12. An overtube according to claim 11, wherein:
    said sleeve comprises one of polyisoprene and latex.

13. An overtube according to claim 1, in combination with said endoscope, wherein when said endoscope extends through said hub assembly and said fluid is provided under pressure through said fluid connector, said sleeve distends radially inward to form a seal about said endoscope.

14. An overtube for use with an endoscope having an exterior surface and for insertion through a patient's natural body orifice, said overtube comprising:
    a) a tubular member having a proximal portion and a distal portion, and a length therebetween sufficient to extend from a patient's mouth to a patient's stomach, said tubular member defining a central passage for receiving the endoscope therethrough; and
    b) a hub assembly coupled to said proximal portion, said hub assembly including
       a rigid body member having a first end, a second end, an inner surface defining a smooth central passage, an exterior surface, and a fluid connector,
       a flexible sleeve extending within said central passage of said body member, said sleeve having an outer surface, an inner surface, and first and second ends, said first and second ends coupled relative to said body member, with said first end of the sleeve provided everted onto the exterior surface of the body member, and said outer surface of said sleeve and said inner surface of said body member are in communication with said fluid connector,
       an inner collar partly extending into said proximal portion of said tubular member,
       an outer collar extending over said proximal portion of said tubular member and said inner collar to engage said proximal portion of said tubular body to dispose the proximal portion between said inner and outer collars, said outer collar further coupled to said first end of said body member, said inner collar coupled in a snap-fit engagement to said first end of said body member to lock said first end of said flexible sleeve in place, and said inner and outer collars are coupled in a snap-fit engagement to fix said proximal portion of said tubular member therebetween, and a proximal hub collar defining a proximal mouth through said hub, said hub collar coupled to said second end of said body member, wherein when a fluid is provided under pressure through said fluid connector, said sleeve distends radially inward to define an opening smaller than said central passage such that when the endoscope is inserted through the hub and the sleeve distends to define the second diameter, the sleeve is provided in contact about the exterior surface of the endoscope.

15. An overtube according to claim 14, wherein:

said outer collar is coupled in a snap-fit engagement to said inner collar, and said hub collar is coupled in a snap-fit engagement to said second end of said body member.

16. An overtube according to claim 15, wherein:

said inner collar includes an external barb that is inserted into said proximal end of said tubular member.

17. An overtube according to claim 14, wherein:

said inner collar includes a circumferential retaining groove, and said outer collar includes catches that engage said retaining groove of said inner collar to couple said inner and outer collars in said snap-fit engagement.

18. An overtube according to claim 15, wherein:

said inner collar has a proximal flange including a plurality of radially displaced engagement windows, and said first end of said body member includes a plurality of catch barbs that engage within said engagement windows to couple said inner collar and said body member in a snap-fit engagement.

19. An overtube according to claim 15, wherein:

said hub collar includes a plurality of radially displaced engagement windows, and said second end of said body member includes a plurality of catch barbs that engage within said engagement windows of said hub collar to couple said hub collar and said body member in a snap-fit engagement.

20. An overtube according to claim 14, wherein:

said body member is longitudinally symmetrical.

21. An overtube according to claim 14, wherein:

said tubular member is reinforced to remain patent and longitudinally stiff during insertion into the natural orifice, while remaining sufficiently laterally flexible for insertion through a non-straight natural orifice.

22. An overtube according to claim 14, in combination with said endoscope, wherein when said endoscope extends through said hub assembly and said fluid is provided under pressure through said fluid connector, said sleeve distends radially inward to form a seal about said endoscope.

* * * * *